United States Patent [19]

Casey et al.

[11] Patent Number: 5,071,809
[45] Date of Patent: Dec. 10, 1991

[54] TERTIARY AMINE CATALYSTS FOR POLYURETHANES

[75] Inventors: Jeremiah P. Casey, Emmaus; Richard V. C. Carr, Allentown; George J. Wasilczyk, Allentown; Robert G. Petrella, Allentown, all of Pa.

[73] Assignee: Air Products and Chemicals, Inc., Allentown, Pa.

[21] Appl. No.: 519,711

[22] Filed: May 7, 1990

[51] Int. Cl.$^5$ ............................................... B01J 27/24
[52] U.S. Cl. ...................... 502/155; 521/50; 521/115; 521/118; 521/166; 502/167
[58] Field of Search .............. 528/53; 252/426, 431 C; 521/50, 118, 115, 166

[56] References Cited

U.S. PATENT DOCUMENTS 3,492,330  1/1970  Trecker et al. .................... 156/310
4,038,210  7/1977  Rosemund et al. .................... 528/53

OTHER PUBLICATIONS

"C$_4$-Diol Chain Extenders in Castable and Rim Urethanes", Lin, I. et al., J. Elastomers and Plastics, vol. 15 (Apr. 1983), pp. 57-80.

Birch, S. et al., J. Org. Chem., vol. 21, pp. 970-974 (1956).

Primary Examiner—John Kight, III
Assistant Examiner—Duc Truong
Attorney, Agent, or Firm—Russell L. Brewer; James C. Simmons; William F. Marsh

[57] ABSTRACT

The invention pertains to tertiary amines used as catalysts for the preparation of polyurethane foams prepared via the catalytic reaction of a polyisocyanate with a polyol in the presence of blowing agents, etc. The tertiary amine catalysts are prepared by reacting an olefinic nitrile with aliphatic polyol having at least secondary hydroxyl functionality in a ratio less than stoichiometric for providing cyanoalkylated polyol having residual hydroxyl functionality. The resulting cyanoalkylated polyol then is reacted with a secondary amine under conditions for effective reductive alkylation.

The tertiary amine catalysts, because of residual secondary hydroxyl functionality, provide for uniform dispersion within a polyurethane formulation; they provide for additional or extended pot life in polyurethane formulations at temperatures below reaction condition, and they are bound by reaction on cure.

5 Claims, No Drawings

TERTIARY AMINE CATALYSTS FOR POLYURETHANES

FIELD OF THE INVENTION

This invention pertains to tertiary amine catalysts which are suited for catalyzing polyurethane foam formation and the resulting foams.

BACKGROUND OF THE INVENTION

Polyurethane foams are widely known and used in automotive, housing and other industries. Foam is generally referred to as rigid, microcellular, or flexible. Typically, in the preparation of polyurethane foams, a tertiary amine catalyst is used to accelerate the reaction of the polyisocyanate with water to generate carbon dioxide as a blowing agent and to accelerate the reaction of polyols to promote gelling of the reaction. Tertiary amines generally are malodorous and offensive and many have high volatility due to low molecular weight.

Representative patents showing the use of various tertiary amines for polyurethane foams are as follows:

U.S. Pat. No. 2,941,967 discloses tertiary amine catalytic systems containing aliphatically bound ether oxygen atoms having singular and bis functional tertiary amine units. Representative tertiary amines include dimethyl-(2-methoxy-ethyl)amine and 1,4-bis-(3'-dimethylaminopropoxy) butane.

U.S. Pat. No. 4,186,254 discloses alkoxylated derivatives of tertiary amines represented by the formula:

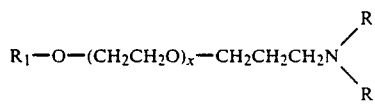

wherein R and $R_1$ are lower alkyl and x is 0–2.
formed by condensing an alkoxy amine with formaldehyde and a lower alkanol and then hydrogenating the resultant product. Representative alkoxylated amines include methoxyethoxypropylamine.

U.S. Pat. No. 4,122,038 discloses the manufacture of polyurethane foams using a catalyst represented by the formula:

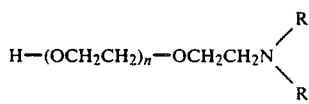

wherein R are lower alkyl which are formed by reacting an alkanolamine with an alkylene oxide as, for example, dimethylethanolamine with ethylene oxide to produce 2-(2-dimethylaminoethoxy) ethanol.

U.S. Pat. No. 4,510,269 discloses tertiary amine catalyst systems which are poly(dialkylaminoalkyl) ethers. These are represented by the general formula:

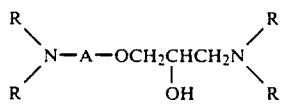

wherein R is lower alkyl and A is a straight chain hydrocarbon. Secondary amines or dialkylamino alcohols are reacted with epihalohydrins. The advantage of the catalyst systems is that they have low vapor pressure, minimal smell, chemically bond with the urethane during the reaction and do not impair the stability of the completed polyurethane part.

U.S. Pat. No. 4,350,778 discloses the preparation of tertiary amines containing secondary alcohol functionality by reacting bis-dimethylaminopropylamine with propylene oxide.

U.S. Pat. No. 4,590,223 discloses the preparation of tertiary amines containing secondary alcohols by reacting N-alkyl piperazines with an alkylene oxide.

SUMMARY OF THE INVENTION

This invention pertains to tertiary amine catalysts containing secondary alcohol functionality for use in preparing polyurethane systems and to the polyurethane foams. The tertiary amines containing secondary alcohol functionality are prepared by reacting an olefinic nitrile, such as acrylonitrile, with an aliphatic polyol having at least one secondary hydroxyl functionality, followed by reductive alkylation of the resulting cyanoalkylated polyol with a secondary aliphatic or cycloaliphatic amine, including those containing hetero atoms. The mole ratio of olefinic nitrile to aliphatic polyol is such that at least one equivalent hydroxyl group per molecule of product remains after reaction.

There are several advantages associated with the tertiary amine catalysts and the urethane foams of the present invention, and these include:

the candidate catalysts have predominantly secondary hydroxy groups available for covalent bond formation as a chain terminator in the polyurethane foam compared to catalysts having more reactive primary hydroxy groups;

the catalysts show excellent stain resistance;

there is an ability to vary tertiary amine level in the catalysts to meet reactivity and volatility requirements while maintaining secondary alcohol reactivity to immobilize the catalyst in the polyurethane matrix; and an ability to control catalytic activity through the type of tertiary amine functionality incorporated into the catalyst via reductive alkylation.

DETAILED DESCRIPTION OF THE INVENTION

In preparing the tertiary amine catalysts of the present invention, an olefinic nitrile, i.e., from 3 to 5 carbon atoms in the structure is reacted with an aliphatic polyol having from 3 to 8 carbon atoms wherein the polyol has at least one secondary alcohol functionality. Representative olefinic nitriles suited for cyanoalkylation of the aliphatic polyol include acrylonitrile and methacrylonitrile.

Aliphatic polyols suited for reaction with the olefinic nitrile are, as stated, those polyols, preferably diols and triols, having from 3 to 8 carbon atoms in the structure. In many instances the aliphatic polyols have both primary and secondary hydroxyl functionality. A preferred diol is 1,2-butanediol because in a 1,2-butanediol system there is high regioselectivity thus generating a greater amount of secondary alcohol in the final product than would be available from cyanoethylation of a less differentially reactive diol such as 1,2-propanediol. Aliphatic polyols suited for reaction with the olefinic nitrile include diols such as 1,2-propanediol; 3-methyl-1,2-butanediol; 3,3-dimethyl-1,2-butanediol; 1,2-pentanediol; 1,2-hexanediol; 1,3-hexanediol; and triols such as glycerin; 1,2,4-butanetriol; 1,3,5-pentanetriol; 1,2,6-hexanetriol and the like, can be utilized.

The cyanoalkylation reaction of the olefinic nitrile with the aliphatic polyol is carried out under conditions typical for cyanoethylation, e.g., at temperatures ranging from 40° to 70° C. and pressures ranging from 0 to 15 psig. The mole ratio of olefinic nitrile to polyol is such that at least one equivalent hydroxy group remains after cyanoethylation. For example, in the synthesis of a cyanoethylated diol a 1 to 1 mole ratio of olefinic mononitrile to diol is used, whereas in the synthesis of a cyanoethylated triol a 1 to 1 and preferably a 2:1 mole ratio of olefinic mononitrile to triol, e.g. glycerin can be used. When a 1:1 mole ratio is used, crosslinking of the catalyzed polyurethane can occur through the two remaining hydroxyl groups.

If an aliphatic polyol having both primary and secondary hydroxy functionality is used, the reaction product will comprise a mixture of cyanoalkoxy alkanols. However, the predominant portion, e.g., greater than about 60% by weight, will be a cyanoalkylated polyol containing secondary hydroxy functionality with the balance consisting of cyanoalkylated polyol containing primary hydroxy functionality. In the case where 1,2 butanediol is the reactant, the normalized monocyanoethylated reaction product will comprise from about 60 to 95% by weight of 1-cyanoethoxy-2-butanol and from about 5 to 40% by weight of 2-cyanoethoxy-1-butanol.

After the cyanoalkylated polyol product is formed, it is reacted with a secondary amine under conditions for effecting reductive alkylation. Under these conditions the resulting cyano groups are converted to tertiary amine groups. This approach permits selection of a wide variety of pendant tertiary amine functionality for the catalyst system. Reductive alkylation is carried out in the presence of hydrogen at hydrogen pressures ranging from 500 to 1500 psig in the presence of a hydrogenation catalyst e.g., nickel, cobalt, palladium and so forth. To avoid cleavage during the reaction, the cyanoalkyated polyol is incrementally added to the secondary amine, or introduced as a co-feed to a fixed bed reactor. The reason for this method of feed addition is to minimize unreacted cyanoalkylated polyol inventory. Unreacted cyanoalkylated polyol present in the system tends to react with amines and/or undergo cleavage to form a variety of by-products. Temperatures for reductive alkylation range from about 50° to 125° C. Total pressures of hydrogen will range from about 500 to 1500 psig.

Representative secondary amines which can be used for reductive alkylation include secondary aliphatic amines, having from 2 to about 12 carbon atoms such as dimethylamine; diethylamine; dipropylamine; di-n-butylamine; diisobutylamine; cycloaliphatic amines; such as N-methylcyclohexylamine; N-ethylcyclohexylamine; N-propylcyclohexylamine; and N-butylcyclohexylamine; and heterocyclic amines which include morpholine; N-methylpiperazine; N-ethylpiperazine, and so forth.

The resulting tertiary amine catalysts are generally represented by the formula:

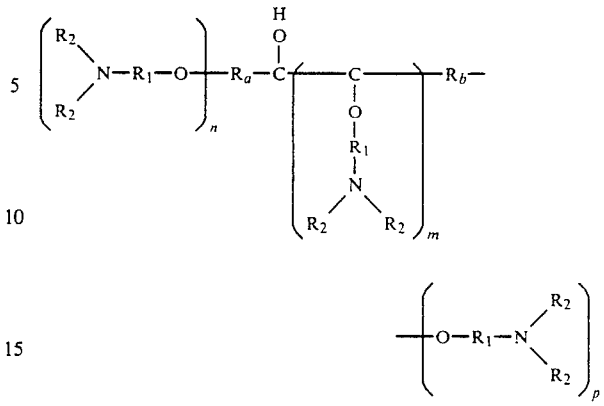

$R_a$ is $C_{1-3}$ alkylene when n is 1 or $R_a$ may be $C_{1-3}$ alkyl or $C_{1-3}$ hydroxyalkyl when n is 0 and p is 1;

$R_b$ is $C_{1-3}$ alkylene when p is 1 or $R_b$ may be $C_{1-3}$ alkyl or $C_{1-3}$ hydroxyalkyl when n is 1 and p is 0;

$R_1$ is $C_{3-5}$ alkylene;

$R_2$ is $C_{1-4}$ lower alkyl, $C_{5-10}$ cycloaliphatic or they are combined to form a 5 to 6 membered ring;

n is 0 or 1;

m is 0 or 1;

p is 0 or 1; and, provided that at least n,m, or p is 1.

Typically, in the above formula n will be 1 or p will be 1.

Polyurethane formulations which can be catalyzed by the tertiary amines of this system comprise the reaction product of a polyisocyanate and a polyol. A prepolymer technique or one shot system may be used. Aliphatic, cycloaliphatic, arylaliphatic and heterocyclic polyisocyanates can be used in preparing the polyurethanes. Examples of polyisocyanates which can be used include isophoronediisocyanate, 2,4-/2,6-toluenediisocyanate and mixtures, meta- and para-phenylenediisocyanate, diphenylmethanediisocyanate, and bis(4-isocyanatocyclohexyl)methane etc.

These catalysts are added to the polyurethane formulation at conventional levels ranging from about 0.1-10, preferably 0.5-2.5 parts by weight per 100 weight parts of polyol used in the formulation. However, the range of catalyst may be adjusted to desired effect.

Representative polyols suited for producing polyurethane foams include both polyether and polyester polyols which typically have molecular weights ranging from about 250 to 10,000. Representative polyethers are alkylene oxide adducts of short chain diols, e.g., of ethylene and propylene oxide adducts of ethylene glycol, propylene glycol and butylene glycol, as well as polyols such as glycerin and sorbitol. Others include polytetramethylene glycol (PTMG). Polyester polyols can also be used and are typically prepared by reacting polyhydric alcohol adducts of alkylene oxides with multibasic carboxylic acids, such as adipic acid, succinic acid, phthalic acid, terephthalic acid, and maleic acid.

There are many optional ingredients that can be used in forming polyurethane foams and these optional ingredients typically include blowing agents, such as ethers e.g. dimethyl ether and fluorinated hydrocarbons, e.g., monofluorotrichloromethane, and other catalysts such as organic metallic compounds, e.g., dibutyltin dilaurate. Types and levels of these adducts in polyurethane formulations are well known.

The following examples are intended to represent various embodiments of the invention and are not intended to restrict the scope thereof.

EXAMPLE 1

Preparation of Mixture of 1-Cyanoethoxy-2-butanol / 2-Cyanoethoxy-1-butanol

Into a 2 liter 3-necked round bottomed flask equipped with pressure equalizing dropping funnel, reflux condenser, and magnetic stirring bar was added 1177 g (13.08 moles) of 1,2-butanediol and 3.5 g of anhydrous lithium hydroxide. The solution was heated to 40° C. with stirring and then 570 g (10.75 moles) of acrylonitrile was added dropwise over a period of 2 hours and 45 minutes. The mixture then was allowed to react an additional one hour at temperature.

The cooled product was neutralized with 50 g of Amberlyst XN-1010 ion exchange resin, filtered and analyzed by GC to be 20.9% 1,2-butanediol, 62.3% 1-cyanoethoxy-2-butanol, 10.2% 2-cyanoethoxy-1-butanol, and 6.7% 1,2-dicyanoethoxybutane.

EXAMPLE 2

Preparation of 1-(3-Dimethylaminopropoxy)-2-butanol/ 2-(3-Dimethylaminopropoxy)-1-butanol Into a two liter stainless steel autoclave was placed 138 g of 5% palladium on carbon (50% water wet). The autoclave was sealed, pressurized/purged three times with nitrogen and then four times with hydrogen. With the reactor at one atmosphere hydrogen pressure. 291 g (6.45 moles) anhydrous dimethylamine was charged from a cylinder; the reactor ambient pressure at 18° C. was 16 psi. The reactor was then pressurized with hydrogen to 600 psi. The reaction mixture was heated to 63° C. while being stirred at 500 rpm. While maintaining this temperature, the reactor was pressurized with hydrogen to 1000 psi and maintained by means of a regulated hydrogen ballast tank. 879 g (3.81 moles) of the acrylonitrile adduct of 1,2-butanediol, i.e., the cyanoethoxybutanol mixture from Example 1 was pumped to the reactor at an initial rate of 7.7 ml/min, or 0.047 moles/min at a stirrer rate of 1250 rpm. Initially the hydrogen uptake (2 moles hydrogen per mole of nitrile) measured against a ballast tank at STP was less than theoretical. Therefore, the feed pump was turned off to permit the consumption of excess nitrile in the reactor. At this time, the reaction temperature was raised to 83° C. resulting in a hydrogen uptake. The feed pump was started and after one-half of the feed was pumped, (440 g) the feed pump was shut off and the hydrogen uptake allowed to baseline. At baseline, the initial 7.7 ml/min feed rate was restarted. After the entire addition of the feed, 30 min were necessary for hydrogen uptake to cease.

The reaction product was cooled, vented of hydrogen and any ammonia produced, and then purged with nitrogen. The crude reaction product was removed from the reactor, filtered free of catalyst, and analyzed by capillary gas chromatography. The colorless reaction crude was concentrated by distilling off the methanol rinse solvent, unreacted 1,2-butanediol, and lights by rotary evaporation at 53 mm of Hg vacuum at 90° C.; the material was liquid and colorless. This solvent-stripped crude product was fractionally vacuum distilled through a 54"×1" packed column at 25 mm Hg with a bp of 132° C. (pot at 145° C.). The final product was a liquid at room temperature and colorless with a distilled purity of 100% by capillary gas chromatography flame ionization detection (95% primary adduct, 5% secondary adduct).

EXAMPLE 3

Preparation of 1-(3-(N-methylpiperazino)-propoxy)-2-butanol/ 2-(3-(N-methylpiperazino)propoxy)-1-butanol Into a two liter stainless steel autoclave was placed 140 g of 5% palladium on carbon (50% water wet) and 765 g (7.5 moles) 1-methylpiperazine. The autoclave was sealed, pressurized/purged three times with nitrogen, then four times with hydrogen. The reactor was then pressurized with hydrogen to 600 psi. The reaction mixture was heated to 60° C. while being stirred at 800 rpm. While maintaining this temperature, the reactor was pressurized with hydrogen to 1050 psi. While maintaining reactor pressure by means of a regulated hydrogen ballast tank, 644 g (4.5 moles) of the acrylonitrile adduct of 1,2-butanediol was pumped to the mixture at an initial rate of 2.8 g/min, or 0.02 moles/min. Initially, there was no hydrogen uptake (2 moles hydrogen per mole of nitrile theoretical) measured off a ballast tank at STP. Therefore, the feed pump was turned off and the reaction temperature raised to, ultimately, 123° C., resulting in hydrogen uptake to permit the consumption of excess nitrile build-up. At this time, the feed pump was started. After one-third addition of the feed, the reaction temperature was gradually reduced to 100° C. for the remainder of the reductive amination. An additional 75 minutes of run time were necessary for hydrogen uptake to cease.

The reaction mixture was cooled, vented of hydrogen and the ammonia produced, and purged with nitrogen. The reaction crude was removed from the reactor, filtered free of catalyst, and analyzed by capillary gas chromatography. The yellow reaction crude was concentrated by distilling off the methanol rinse solvent, and some of the unreacted 1,2-butanediol and lights by rotary evaporation at 53 mm of $H_g$ and 70° C.; the material was liquid and slightly turbid. This solvent-stripped crude product was fractionally vacuum-distilled through a 26"×1" packed column at 11 mm of Hg with a boiling point of 163° C. (pot at 195° C.). The final product was a liquid at room temperature and colorless with a distilled purity of 97.4% by capillary gas chromatography flame ionization detection (91.6% primary adduct, 5.8% secondary adduct).

EXAMPLE 4

Polyurethane Foams Catalyzed With Dimethylaminopropoxybutanols

A polyurethane foam was prepared in conventional manner. The polyurethane formulation used to demonstrate catalyst performance via reactivity in foam formation in weight parts was:

| | | |
|---|---|---|
| Voranol 4701 - polyol | 83 | parts |
| Niax 34-28 - polyol | 17 | parts |
| Poly-G 70-600 - polyol | 2.6 | parts |
| Triethanolamine | 0.87 | parts |
| B-4113 | 0.44 | parts |
| Water | 2.2 | parts |
| PAPI 901 | @ 100 | index. |

Voranol 4701 is a high molecular weight (3000-5000) propylene oxide triol that is end capped with ethylene oxide to provide primary hydroxyl functionality and sold by Dow Chemical Co. It provides polymer backbone and foam flexibility.

Niax 34-28 is a styrene/acrylonitrile graft copolymer with 22 weight % graft on a high molecular weight triol with primary alcohol functionality sold by Union Carbide Corporation., it provides desirable load-bearing characteristics to the foam.

Poly G 70-600 is a low molecular weight polyfunctional polyol that provides foam rigidity and some load building properties and is sold by Olin Corp.

Triethanolamine is a trifunctional crosslinker used to provide early stability to the rising foam and helps limit foam flexibility.

B-4113 is a silicone surfactant used to stabilize the foam during rise and is sold by Goldschmidt Corp..

Water is used as the blowing agent to generate carbon dioxide. PAPI 901 is a modified methylenediphenyldiisocyanate of 280 molecular weight with 31 weight % NCO designed for use in semi-flexible and integral skin foams.

The foam reactivity rise was measured using the following candidate catalysts consisting of:

DMAPB which is the mixture of 1-(3-dimethylaminopropoxy)-2-butanol / 2-(3-dimethylaminopropoxy)-1- butanol from Example I; N,N-dimethylethanolamine (DMEA) and N,N-dimethylaminoethyl-N'-methylethanolamine (DEME). The latter two are commercial catalysts.

Table 2 sets forth conditions and results.

TABLE 2

| CATALYST | DMEA | DEME | DMAPB |
|---|---|---|---|
| Level (parts) | 1.5 | 1.0 | 1.8 |
| Cream time (sec) | 10 | 14 | 17 |
| String gel time (sec) | 48 | 59 | 49 |
| Full rise time (sec) | 88 | 96 | 80 |
| Tack free time (sec) | 365 | 300 | 180 |

Times cited are from mixing of the polyol masterbatch with isocyanate. The uniqueness of the candidate catalyst is that it exhibits a delay in the start of the foaming reaction but reaches final reaction quickly compared to the commercial controls. Both are desirable traits. The long cream time allows more time for the wet chemicals, the masterbatch isocyanate mixture, to flow through a mold before foam formation starts. The faster final cure increases productivity.

EXAMPLE 5

Vinyl Staining Resistance

A lab test used for vinyl staining resistance is to place vinyl sheeting molded onto a foam core in an oven at 30020 F. This test is intended to simulate the conditions afforded polyvinyl chloride-covered foamed dashboards which are exposed to solar heating given rakish windshield design. Upon elevated vinyl/foam temperatures distillation of the amine catalysts from the foam occurs causing dehydrohalogenation and blackening of the polyvinyl chloride.

Table 3 sets forth conditions and results for vinyl staining resistance. Hours to onset of staining for the formulation cited above were:

TABLE 3

| CATALYST | DMEA | DEME | DMAPB |
|---|---|---|---|
| Hours to stain onset | 15.0 | 14.0 | 27.0 |

The above data show the much longer time to stain the vinyl when utilizing the tertiary amine catalysts described herein.

What is claimed is:

1. In a polyurethane composition formed by the reaction of a polyisocyanate with a polyol in the presence of a tertiary amine catalyst, the improvement which comprises utilizing the tertiary amine catalyst represented by the formula:

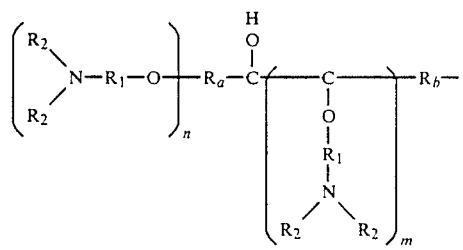

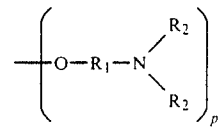

$R_a$ is $C_{1-3}$ alkylene when n is 1 or $R_a$ may be $C_{1-3}$ alkyl or $C_{1-3}$ hydroxyalkyl when n is 0 and p is 1;

$R_b$ is $C_{1-3}$ alkylene when p is 1 or $R_b$ may be $C_{1-3}$ alkyl or $C_{1-3}$ hydroxyalkyl when n is 1 and p is 0;

$R_1$ is $C_{3-5}$ alkylene;

$R_2$ os $C_{1-4}$ lower alkyl, $C_{5-10}$ cycloaliphatic or the two $R_2$ groups may be combined to form a 5 to 6 membered ring;

n is 0 or 1;

m is 0 or 1;

p is 0 or 1; and, provided that at least n,m, or p is 1.

2. The polyurethane composition of claim 1 wherein the tertiary amine catalyst comprises 1-(3-dialkylaminopropoxy)-2-butanol.

3. The polyurethane composition of claim 2 wherein the tertiary amine is 1-(3-dimethylaminopropoxy)-2-butanol.

4. The polyurethane composition of claim 1 wherein the tertiary amine is 1-(3-(N-methylpiperazino)-propoxy)-2-butanol.

5. The polyurethane composition of claim 1 wherein the tertiary amine catalyst is 1-(morpholinopropoxy)-2-butanol.

* * * * *